United States Patent [19]

Kaufmann et al.

[11] Patent Number: 5,334,724

[45] Date of Patent: * Aug. 2, 1994

[54] PREPARATION OF SUBSTITUTED 2-CHLOROPYRIDINES

[75] Inventors: Dieter Kaufmann, Bergisch-Gladbach; Klaus Jelich, Wuppertal; Rudolf Braden, Odenthal; Winfried Rosen, Wuppertal, all of Fed. Rep. of Germany

[73] Assignee: Bayer Aktiengesellschaft, Leverkusen, Fed. Rep. of Germany

[*] Notice: The portion of the term of this patent subsequent to Apr. 7, 2009 has been disclaimed.

[21] Appl. No.: 905,080

[22] Filed: Jun. 24, 1992

Related U.S. Application Data

[63] Continuation of Ser. No. 639,617, Jan. 10, 1991, abandoned.

[30] Foreign Application Priority Data

Jan. 18, 1990 [DE] Fed. Rep. of Germany ........ 4001248
Jun. 23, 1990 [DE] Fed. Rep. of Germany ........ 4020055

[51] Int. Cl.$^5$ .................. C07D 213/26; C07D 213/61; C07D 213/56; C07D 213/81
[52] U.S. Cl. ..................................... 546/345; 546/168; 546/169; 546/170; 546/283; 546/286; 546/287; 546/323; 546/326
[58] Field of Search ................ 546/345, 283, 286, 287, 546/323, 326, 168, 169, 170

[56] References Cited

U.S. PATENT DOCUMENTS

| 4,628,096 | 12/1986 | Nelson et al. | 546/250 |
| 5,010,201 | 4/1991 | Kauffman et al. | 546/345 |
| 5,099,025 | 3/1992 | Kaufmann et al. | 546/316 |
| 5,103,011 | 4/1992 | Jelich et al. | 546/345 |

FOREIGN PATENT DOCUMENTS

1200304 9/1965 Fed. Rep. of Germany ...... 546/345

OTHER PUBLICATIONS

Abramovitch, Pyridine and Its Derivatives, Supplement Part Two, pp. 111-113, Wiley-Interscience pub. 1974.

Chemical Abstracts, Band 58, Nr. 1, Jan. 7, 1963, Columbus, Ohio U.S.A.
Henecka, "Umwandlung von Carbonsauren", Article, pp. 463-474.
J. F. Vozza, "Reactions of 2-Pincoline 1-Oxide with Reactive Halides", article, vol. 27 (1962), pp. 3856-3860.
H. Yamanaka et al., "Site-Selectivity in the Reaction of S-Substituted . . . ", Chem. Pharm. Bull. (1988) vol. 36, pp. 2244-2247.
27-Heterocycles, vol. 112 (1990) p. 35696.
37-Heterocyclic Compounds, vol. 64 (1966), pp. 5053-5054.

Primary Examiner—Alan L. Rotman
Attorney, Agent, or Firm—Sprung Horn Kramer & Woods

[57] ABSTRACT

A process for the preparation of a substituted 2-chloropyridine derivatives of the formula

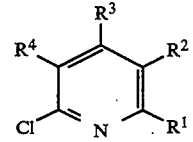

in which
$R^1$, $R^2$, $R^3$ and $R^4$ represent hydrogen or various other radicals, which comprises reacting a pyridine-1-oxide of the formula

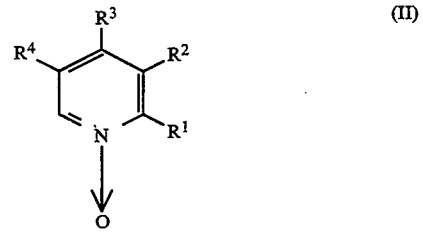

with an aromatic carbonyl chloride in the presence of an inert organic solvent and in the presence of an acid acceptor at a temperature between about −20° C. and 200° C.

13 Claims, No Drawings

PREPARATION OF SUBSTITUTED 2-CHLOROPYRIDINES

This application is a continuation of application Ser. No. 639,617, filed Jan. 10, 1991, abandoned.

The present invention relates to a new process for the preparation of substituted 2-chloropyridines.

It is known that 2-chloro-5-methyl-pyridine is obtained in addition to 2-chloro-3-methyl-pyridine, 4-chloro-3-methyl-pyridine and 3-chloro-5-methyl-pyridine when 3-methyl-pyridine-1-oxide is reacted with phosphoryl chloride (compare Weissberger, Chemistry of Heterocyclic Compounds, Pyridine and its Derivatives, Vol. 14, Supplement, Part 2, p. 112, Publisher John Wiley & Sons, New York, 1974). The principal product of this reaction is 4-chloro-3-methyl-pyridine; the proportion of 2-chloro-5-methyl-pyridine is in general below 25%.

The reaction of 3-methyl-pyridine-1-oxide with phosphoryl chloride in the presence of a basic organic nitrogen compound and in the presence of a diluent is known (German Offenlegungsschrift 3,800,179) and the reaction of substituted pyridine-1-oxides with chlorophosphoric acid esters or chlorophosphoramides in the presence of a basic organic nitrogen compound and in the presence of a diluent is the subject of German Patent Application P 38 39 332.

A new process for the preparation of substituted 2-chloropyridine derivatives of the formula (I)

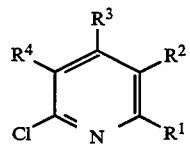

(I)

in which $R^1$ represents hydrogen, fluorine, chlorine, cyano, carbalkoxy ($C_1-C_4$) or

in which $R^5$ and $R^6$ are identical or different and represent hydrogen or alkyl ($C_1-C_4$), $R^2$ represents hydrogen, fluorine, chlorine, alkyl-($C_1-C_4$), halogenoalkyl-($C_1-C_4$), cyanoalkyl-($C_1-C_4$), alkoxy($C_1-C_4$)-alkyl($C_1-C_4$), dialkylamino($C_1-C_4$)alkyl($C_1-C_4$), acyl($C_1-C_4$)-acetal; carbalkoxy($C_1-C_4$) or

in which $R^5$ and $R^6$ are identical or different and represent hydrogen or alkyl ($C_1-C_4$) or in which $R^1$ and $R^2$ together represent the divalent group —CH=CH—CH=CH—, $R^3$ represents hydrogen, chlorine, carbalkoxy($C_1-C_4$) or

in which $R^5$ and $R^6$ are identical or different and represent alkyl ($C_1-C_4$), $R^4$ represents hydrogen, fluorine, chlorine or cyano, or in which $R^3$ and $R^4$ together represent the divalent group —CH=CH—CH=CH—, has now been found.

The new process is characterized in that pyridine-1-oxides of the formula (II)

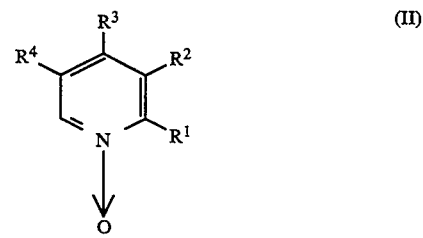

(II)

in which $R^1$, $R^2$, $R^3$ and $R^4$ have the abovementioned meanings, are reacted with an aromatic carbonyl chloride in the presence of an inert organic solvent and in the presence of an acid acceptor at temperatures between −20° C. and 200° C., then optionally reacted with phosgene or thionyl chloride at temperatures between 70° C. and 160° C., and the product obtained is optionally further separated.

If desired, the reaction with phosgene or thionyl chloride is carried out in the presence of an activator.

Surprisingly, it is possible by the process according to the invention to convert substituted pyridine-1-oxides of the formula (II) into the corresponding substituted 2-chloropyridines of the formula (I) in a simple manner and with a low outlay, while achieving surprisingly high yields, by reaction with benzoyl chlorides or phthaloyl chlorides in the presence of an acid acceptor, optionally with post-treatment with phosgene or thionyl chloride.

Advantages of the process according to the invention in addition to the good yield of desired product are also that the proportion of isomeric by-products is substantially lower than in the synthesis methods known hitherto. A further advantage is that the chlorinating agents employed according to the invention are common industrial products, and these can even be recycled again after the chlorination of the pyridine-N-oxides. Furthermore, if desired, the pure compound (I) can easily be prepared from the reaction product by customary/methods, for example by distillative separation or by other customary separation methods.

The process according to the invention thus represents a valuable enrichment of the art.

If 3-methyl-pyridine-1-oxide is reacted with ortho-phthaloyl chloride in methylene chloride in the presence of the base triethylamine, the course of the reaction in the process according to the invention may be outlined by the following equation:

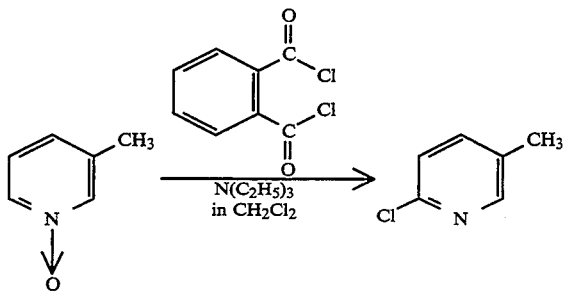

The following may be mentioned as preferred compounds of the general formula (I) which can be prepared by the process according to the invention:
2,3-dichloropyridine
2,4-dichloropyridine
2,6-dichloropyridine
2-chloro-3-cyano-pyridine
2-chloro-6-cyano-pyridine
methyl 6-chloro-pyridine-2-carboxylate
ethyl 6-chloro-pyridine-2-carboxylate
N,N-dimethyl-6-chloro-pyridine-2-carboxamide
N,N-diethyl-6-chloro-pyridine-2-carboxamide
N,N-diethyl-6-chloronicotinamide
methyl 2-chloro-pyridine-4-carboxylate
ethyl 2-chloro-pyridine-4-carboxylate
N,N-dimethyl-2-chloro-pyridine-4-carboxamide
N,N-diethyl-2-chloro-pyridine-4-carboxamide
2-chloro-5-diisopropylaminomethyl-pyridine
2-chloro-5-diisobutylaminomethyl-pyridine
2-chloro-5-methyl-pyridine
2,6-dichloro-3-methyl-pyridine
2,6-dichloro-3-fluoro-5-methyl-pyridine
2-chloro-3,6-difluoro-5-methyl-pyridine
2-chloro-5-ethyl-pyridine
2-chloro-5-chloromethyl-pyridine
2-chloro-5-acetyl-pyridine-ethylene acetal
2,3-dichloro-5-acetyl-pyridine-ethylene acetal
2-chloro-5-cyanomethyl-pyridine
2-chloro-5-methoxymethyl-pyridine
2-chloro-5-ethoxymethyl-pyridine
methyl 6-chloro-nicotinate
ethyl 6-chloro-nicotinate
N,N-dimethyl-6-chloro-nicotinamide
2-chloroquinoline
1-chloroisoquinoline The following compound of the formula (I) is particularly preferably prepared:
2-chloro-5-methyl-pyridine.

The starting materials, pyridine-1-oxides of the formula (II) and benzoyl chlorides or phthaloyl chlorides, are known compounds of organic chemistry or can be prepared by known processes. See, for example: Weissberger, Chemistry of Heterocyclic Compounds, Pyridine and its Derivatives, Vol. 14, Supplement, Part 2, p. 112, Verlag John Wiley & Sons, New York, 1974. Methoden der Organischen Chemie [Methods of Organic Chemistry] (Houben-Weyl, Müller), Volume VIII, p. 463 et seq., Georg Thieme Verlag, Stuttgart, 1952.

Formula (II) provides a general definition of the substituted pyridine-1-oxides employed as starting materials for the process according to the invention.

In the formula (II)

$R^1$ preferably represents hydrogen, fluorine, chlorine, cyano, $COOCH_3$, $COOC_2H_5$, $CON(CH_3)_2$ or $CON(C_2H_5)_2$, $R^2$ preferably represents hydrogen, fluorine, chlorine, $CH_3$, $C_2H_5$, $CH_2Cl$, $CH_2CN$, $CH_2$—$OCH_3$, $CH_2$—$OC_2H_5$, $CH_2$—$N(i$—$C_3H_7)_2$, $CH_2$—$N(i$—$C_4H_9)_2$,

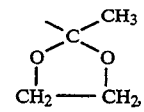

or $R^1$ and $R^2$ in each case together represent the divalent group —CH=CH—CH=CH—, $R^3$ preferably represents hydrogen, chlorine, $COOCH_3$, $COOCH_3$, $COOC_2H_5$, $CON(CH_3)_2$ or $CON(C_2H_5)_2$, $COOC_2H_5$, $CON(CH_3)_2$ or $CON(C_2H_5)_2$, and $R^4$ preferably represents hydrogen, fluorine, chlorine,or cyano, or $R^3$ and $R^4$ in each case together represent the divalent group —CH=CH—CH=CH—.

In particular, 3-methyl-pyridine-1-oxide is employed as a starting material of the formula (II).

The aromatic carbonyl chlorides employed in the process according to the invention are preferably derived from the following compounds or classes of compound:
benzoyl chloride
monochlorobenzoyl chlorides
dichlorobenzoyl chlorides
monomethylbenzoyl chlorides
monochloromethylbenzoyl chlorides
dimethylbenzoyl chlorides
monomethoxybenzoyl chlorides
mononitrobenzoyl chlorides
phthaloyl chlorides
dichlorophthalide
monochlorophthaloyl chlorides
dichlorophthaloyl chlorides
mononitrophthaloyl chlorides
naphthalenecarbonyl chlorides.

Benzoyl chloride and ortho-, meta- and para-phthaloyl chloride are particularly preferably employed.

The process according to the invention is carried out using inert organic solvents. Suitable solvents here are virtually all inert organic solvents. These preferably include aliphatic or aromatic hydrocarbons such as pentane, hexane, heptane, octane, cyclohexane, methylcyclohexane, petroleum ether, benzine, ligroin, benzene, toluene, xylene and tetralin, halogenated hydrocarbons such as methylene chloride, ethylene chloride, trichloroethylene, chloroform, carbon tetrachloride, 1,1,2-trichloroethane, 1,2-dichloropropane, 1,2,3-trichloropropane, chlorobenzene and dichlorobenzene, ethers such as diethyl ether, dipropyl ether, diisopropyl ether, dibutyl ether, methyl tert-butyl ether, methyl tert.-amyl ether, glycol dimethyl ether, diglycol dimethyl ether, tetrahyrofuran and dioxane and anisole, ketones such as acetone, methyl ethyl ketone, diethyl ketone, methyl isopropyl ketone, methyl isobutyl ketone and methyl tert.-butyl ketone, esters such as methyl acetate, ethyl acetate, propyl acetate, butyl acetate, amyl acetate, dimethyl phthalate and diethyl phthalate, nitriles such as acetonitrile and propionitrile, amides such as dimethylformamide, dimethylacetamide and N-methylpyrrolidone and also dimethyl sulphoxide and tetramethylene sulphone.

Methylene chloride, ethylene chloride, chloroform, 1,1,2-trichloroethane, 1,2-dichloropropane, 1,2,3-trichloropropane and chlorobenzenes are particularly preferred as organic solvents.

Basic organic nitrogen compounds are preferably employed in the process according to the invention as acid acceptors: thus trialkylamines such as, for example, trimethylamine, triethylamine, tripropylamine, tributylamine and diazabicyclooctane, dialkylcycloalkylamines such as, for example, dimethyl-cyclopentylamine, diethyl-cyclopentylamine, dimethyl-cyclohexylamine and diethyl-cyclohexylamine, dialkyl-aralkylamine such as, for example, dimethylbenzylamine and diethylbenzylamine.

Triethylamine is particularly preferred as a basic organic nitrogen compound.

In the process according to the invention, the reaction is carried out in a temperature range between −20° C. and 200° C., preferably at temperatures between 0° C. and 160° C. The process according to the invention is in general carried out under normal pressure. However, it is also possible to work at elevated or reduced pressures of between 0.1 and 10 bar. In order to carry out the process according to the invention, between 1 and 10 moles, preferably between 1 and 2 moles, of aromatic carbonyl chloride and also between 1 and 10 moles, preferably between 1 and 2 moles of the acid acceptor, preferably of the basic organic nitrogen compound, are in general employed per mole of substituted pyridine-1-oxide of the formula (II). The use of approximately 1.5 moles each of aromatic carbonyl chloride and nitrogen compound per mole of substituted pyridine-1-oxide is particularly preferred. When working in chlorobenzenes, it is advantageous subsequently to react further with phosgene or thionyl chloride to obtain a higher yield. In order to carry out this process step according to the invention, between 1 and 10 moles, preferably between 2 and 5 moles, of phosgene or thionyl chloride are in general employed per mole of substituted pyridine-1-oxide of the formula (II); the use of 2 to 4 moles of phosgene is particularly preferred. The phosgene and the thionyl chloride may optionally be activated by addition of a catalytically active activator. Compounds of the formamides class are preferred for this purpose and N,N-dibutylformamide or N-methylformanilide or distearylformamide is particularly preferably added.

To carry out the process according to the invention in the preferred manner, the aromatic carbonyl chloride is added dropwise to a solution of the substituted pyridine-1-oxide of the formula (II) and the basic organic nitrogen compound, and the complete reaction mixture is stirred for several hours at the respective temperature (preferably in the range from 40° to 160° C.). When working in chlorobenzenes, a formamide is subsequently added in order to carry out the process according to the invention in the preferred manner and phosgene is introduced for several hours at the respective temperature (preferably in the range from 70° to 150° C.) or thionyl chloride is added dropwise. When working in chlorobenzene a temperature of 120° to 140° C. is particularly preferred.

Working-up can be carried out in the customary manner. Preferably, the hydrochloride formed from the basic organic nitrogen compound is first filtered off; it can be recycled again after alkaline cleavage. The organic solvent is then preferably removed - for example by distillation, the bottom is adjusted to pH 6 with an aqueous alkali metal or alkaline earth metal hydroxide solution such as, for example, sodium hydroxide solution and the reaction product is substantially removed therefrom by steam distillation. The organic portion of the steam distillate essentially contains the product of the formula (I).

The preparation of the compound of the formula (I) in pure form from the organic portion of the steam distillate can be carried out by customary methods, for example by a fine distillation in a packed column. The total yield in the preparation of 2-chloro-5-methylpyridine is 60 to 85% of theory, starting from 3-methylpyridine-1-oxide.

The 2-chloro-5-methyl-pyridine which can be prepared by the process according to the invention is known as an intermediate for pharmaceuticals (compare DE-A 2,812,585).

Furthermore, 2-chloro-5-methyl-pyridine can be employed advantageously as an intermediate for the preparation of insecticidal nitromethylene derivatives (compare EP-A 163,855).

Preparation Example 1

2-Chloro-5-methyl-pyridine 76.1 g (0.375 mol) of o-phthaloyl chloride are added dropwise under nitrogen to a solution of 27.3 g (0.25 mol) of 3-methylpyridine-1-oxide and 37.9 g (0.375 mol) of triethylamine in 250 ml of methylene chloride in the course of 45 min in such a way that gentle reflux occurs. The mixture is subsequently heated under reflux for a further 2 hours, and the precipitate is filtered off with suction, the filter cake is washed with 50 ml of methylene chloride and the solvent is removed by distillation. The bottom is subjected to steam distillation, the pH of 6 being maintained by continuously adding 45% strength sodium hydroxide solution. The distillate is extracted three times using 100 ml of methylene chloride each time and the extracts are fractionally distilled.

Yield: 27.1 g (85%) of a mixture of 84% of 2-chloro-5-methylpyridine and 16% of 2-chloro-3-methyl-pyridine.

The structure is checked by $^1$H-NMR spectra.

$^1$H-NMR (CDCl$_3$, 200 MHz): δ=8.16 (6-H, ddq), 7.43 (4-H, ddq), 7.16 (3-H, br. d), 2.26 ppm (CH$_3$, br. s).

Pure 2-chloro-5-methyl-pyridine can be separated off by fractional distillation.

Preparation Example 2

2-Chloro-5-methyl-pyridine 76.1 g (0.375 mol) of o-phthaloyl chloride are added dropwise under nitrogen to a solution of 27.3 g (0.25 mol) of 3-methylpyridine-1-oxide and 37.9 g (0.375 mol) of triethylamine in 250 ml of chlorobenzene in the course of 30 min. The mixture is subsequently heated under reflux for 2.5 hours, then the precipitate is filtered off with suction and the filter cake is washed with 50 ml of chlorobenzene. After adding 2 ml of N,N-dibutylformamide, 98.9 g (1 mol) of phosgene is introduced at 120° C. in the course of 2 hours. The mixture is allowed to cool, stirred for 30 min with 200 ml of concentrated hydrochloric acid and neutralized with 45% strength sodium hydroxide solution, the aqueous phase is extracted three times with 100 ml of toluene each time and the toluene phase is fractionated.

Yield: 22.3 g (70%) of a mixture of 85% of 2-chloro-5-methylpyridine and 15% of 2-chloro-3-methyl-pyridine.

Pure 2-chloro-5-methyl-pyridine can be separated off by fractional distillation.

Preparation Example 3

2-Chloro-5-methyl-pyridine 52.7 g (0.375 mol) of benzoyl chloride are added dropwise under nitrogen to a solution of 27.3 g (0.25 mol) of 3-methylpyridine-1-oxide and 37.9 g (0.375 mol) of triethylamine in 250 ml of methylene chloride in the course of 45 min. The mixture is subsequently heated under reflux for a further 3 hours and then filtered, the filter cake is washed with 50 ml of methylene chloride and the solvent is removed by distillation. The bottom is subjected to steam distillation, the pH of 6 being maintained by continuously adding 45% strength sodium hydroxide solution. The distillate is extracted three times using 100 ml of methylene chloride each time and the extracts are fractionally distilled.

Yield: 21.7 g (68%) of a mixture of 87% of 2-chloro-5-methylpyridine and 13% of 2-chloro-3-methyl-pyridine.

Pure 2-chloro-5-methyl-pyridine can be separated off by fractional distillation.

Preparation Example 4

2-Chloro-5-methyl-pyridine 52.7 g (0.375 mol) of benzoyl chloride are added dropwise under nitrogen to a solution of 27.3 g (0.25 mol) of 3-methylpyridine-1-oxide and 37.9 g (0.375 mol) of triethylamine in 250 ml of chlorobenzene in the course of 30 min. The mixture is subsequently heated under reflux for 3 hours, the precipitate is filtered off with suction and the filter cake is washed with 50 ml of chlorobenzene. After adding 2 ml of N,N-dibutylformamide, 98.9 g (1 mol) of phosgene is introduced at 120° C. in the course of 2 hours. The mixture is allowed to cool, stirred for 30 min with 200 ml of conc. hydrochloric acid and neutralized with 45 per cent sodium hydroxide solution, the aqueous phase is extracted three times using 100 ml of toluene each time and the toluene phase is fractionated.

Yield: 19.1 g (60%) of a mixture of 86% of 2-chloro-5-methylpyridine and 14% of 2chloro-3-methylpyridine.

Pure 2chloro-5-methyl-pyridine can be separated off by fractional distillation.

Preparation Example 5

2-Chloro-5-methyl-pyridine 76.1 g (0.375 mol) of o-phthaloyl chloride are added dropwise under nitrogen to a solution of 27.3 g (0.25 mol) of 3-methylpyridine-1-oxide and 37.9 g (0.375 mol) of triethylamine in 250 ml of 1,2-dichloropropane in the course of 45 min. The mixture is subsequently heated under reflux for a further 4 hours, the precipitate is then filtered off with suction, the filter cake is washed with 50 ml of 1,2-dichloropropane and the solvent is removed by distillation. The bottom is subjected to steam distillation, the pH of 6 being maintained by continuously adding 45 per cent sodium hydroxide solution. The distillate is extracted three times using 100 ml of methylene chloride each time and the extracts are fractionally distilled.

Yield: 22.3 g (70%) of a mixture of 84% of 2-chloro-5-methylpyridine and 16% of 2-chloro-3-methylpyridine.

Pure 2-chloro-5-methyl-pyridine can be separated off by fractional distillation.

Preparation Example 6

2-Chloro-5-methyl-pyridine 76.1 g (0.375 mol) of o-phthaloyl chloride are added dropwise under nitrogen to a solution of 27.3 g (0.25 mol) of 3-methylpyridine-1-oxide and 37.9 g (0.375 mol) of triethylamine in 250 ml of 1,2,3-trichloropropane in the course of 45 min. The mixture is subsequently heated at 70° C. for a further 12 hours, then the precipitate is filtered off with suction and the filtered cake is washed with 50 ml of 1,2,3-trichloropropane. The liquid phase is stirred with 100 ml of conc. hydrochloric acid, and the aqueous phase is separated off, neutralized with sodium hydroxide solution and extracted three times using 50 ml of toluene each time; the extracts are fractionally distilled.

Yield: 25.4 g (80%) of a mixture of 84% of 2-chloro-5-methylpyridine and 16% of 2-chloro-3-methylpyridine.

Pure 2-chloro-5-methyl-pyridine can be separated off by fractional distillation.

Preparation Example 7

2-Chloro-5-methyl-pyridine 65.6 g (0.375 mol) of 4-chlorobenzoyl chloride are added dropwise under nitrogen to a solution of 27.3 g (0.25 mol) of 3-methylpyridine-1-oxide and 37.9 g (0.375 mol) of triethylamine in 250 ml of methylene chloride in the course of 35 min. The mixture is subsequently heated under reflux for a further 5 hours, the precipitate is then filtered off with suction, the filter cake is washed with 50 ml of methylene chloride and the solvent is removed by distillation. The bottom is subjected to steam distillation, the pH of 6 being maintained by continuously adding 45 per cent sodium hydroxide solution. The distillate is extracted three times using 100 ml of methylene chloride each time and the extracts are fractionally distilled.

Yield: 21.6 g (68%) of a mixture of 89% of 2-chloro-5-methylpyridine and 11% of 2-chloro-3-methylpyridine.

Pure 2-chloro-5-methyl-pyridine can be separated off by fractional distillation.

Preparation Example 8

2-Chloro-5-methyl-pyridine 76.9 g (0.375 mol) of 2-chloromethyl-benzoyl chloride are added dropwise under nitrogen to a solution of 27.3 g (0.25 mol) of 3-methylpyridine-1-oxide and 37.9 g (0.375 mol) of triethylamine in 250 ml of methylene chloride in the course of 30 min. The mixture is subsequently heated under reflux for a further 5 hours, then the precipitate is filtered off with suction, the filter cake is washed with 100 ml of methylene chloride and the solvent is removed by distillation. The bottom is subjected to steam distillation, the pH of 6 being maintained by continuously adding 45 per cent sodium hydroxide solution. The distillate is extracted three times using 100 ml of methylene chloride each time and the extracts are fractionally distilled.

Yield: 24.8 g (78%) of a mixture of 87% of 2-chloro-5-methylpyridine and 13% of 2-chloro-3-methylpyridine.

Pure 2-chloro-5-methylpyridine can be separated off by fractional distillation.

Preparation Example 9

2-Chloro-5-methyl-pyridine 76.1 g (0.375 mol) of m-phthaloyl chloride are added dropwise under nitrogen to a solution of 27.3 g (0.25 mol) of 3-methylpyridine-1-oxide and 37.9 g (0.375 mol) of triethylamine in 250 ml of methylene chloride in the course of 30 min. The mixture is subsequently heated under reflux for a further 5 hours, then the precipitate is filtered off with suction, the filter cake is washed with 50 ml of methylene chloride and the solvent is removed by distillation. The bottom is subjected to steam distillation, the pH of 6 being maintained by continuously adding 45 per cent sodium hydroxide solution. The distillate is extracted three times using 100 ml of methylene chloride each time and the extracts are fractionally distilled.

Yield: 23.9 g (75%) of a mixture of 89% of 2-chloro-5-methylpyridine and 11% of 2-chloro-3-methylpyridine.

Pure 2-chloro-5-methyl-pyridine can be separated off by fractional distillation.

Preparation Example 10

2-Chloro-5-butyl-pyridine 76.1 g (0.375 mol) of o-phthaloyl chloride are added dropwise under nitrogen to a solution of 37.9 g (0.25 mol) of 3-butylpyridine-1-oxide and 37.9 g (0.375 mol) of triethylaunine in 250 ml of methylene chloride in the course of 30 min. The mixture is subsequently heated under reflux for a further 5 hours, then the precipitate is filtered off with suction, the filter cake is washed with 50 ml of methylene chloride and the solvent is removed by distillation. The bottom is subjected to steam distillation, the pH of 6 being maintained by continuously adding 45 per cent sodium hydroxide solution. The distillate is extracted three times using 100 ml of toluene each time and the extracts are fractionally distilled.

Yield: 32.2 g (76%) of a mixture of 95% of 2-chloro-5-butylpyridine and 5% of 2-chloro-3-butylpyridine.

Preparation Example 11

2,6-Dichloro-3-methyl-pyridine 101.5 g (0.50 mol) of o-phthaloyl chloride in 50 ml of chlorobenzene are added dropwise under nitrogen to a solution of 35.9 g (0.25 mol) of 2-chloro-5-methylpyridine-1-oxide and 50.6 g (0.50 mol) of triethylamine in 200 ml of chlorobenzene in the course of 30 min. The mixture is subsequently heated under reflux for a further 12 hours, then the precipitate is filtered off with suction, the filter cake is washed with 50 ml of methylene chloride and the solvent is removed by distillation. The bottom is subjected to steam distillation, the pH of 6 being maintained by continuously adding 45 per cent sodium hydroxide solution. The distillate is extracted three times using 100 ml of methylene chloride each time, the solvent is removed by distillation and the residue is recrystallized from hexane.

Yield: 32.2 g (68%) of 2,6-dichloro-3-methylpyridine.

What is claimed is:

1. A process for the preparation of a substituted 2-chloropyridine of the formula

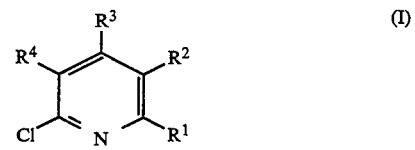

in which

R$^1$ represents hydrogen, fluorine, chlorine, cyano, COOCH$_3$, COOC$_2$H$_5$, CON(CH$_3$)$_2$ or CON(C$_2$H$_5$)$_2$, R$^2$ represents hydrogen, fluorine, chlorine, CH$_3$, C$_2$H$_5$, CH$_2$Cl, CH$_2$CN, CH$_2$—OCH$_3$, CH$_2$—OC$_2$H$_5$, CH$_2$—N(i—C$_3$H$_7$)$_2$, CH$_2$—N(i—C$_4$—H$_9$)$_2$,

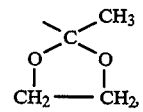

or in which R$^1$ and R$^2$ together represent the divalent group —CH=CH—CH=CH—, R$^3$ represents hydrogen, chlorine, COOCH$_3$, COOC$_2$H$_5$, CON(CH$_3$)$_2$ or CON(C$_2$H$_5$)$_2$, and R$^4$ represents hydrogen, fluorine, chlorine or cyano, or in which R$^3$ and R$^4$ together represent the divalent group —CH=CH—CH=CH—, which comprises reacting a pyridine-1-oxide of the formula

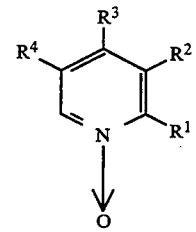

with an aromatic carbonyl chloride in the presence of an inert organic solvent and in the presence of an organic acid acceptor at a temperature between about −20° C. and 200° C., provided that only one of R$^1$, R$^2$, R$^3$ and R$^4$ can represent cyano or carbalkoxy at one time.

2. A process according to claim 1, wherein the aromatic carbonyl chloride is selected from the group consisting of benzoyl chloride, monochlorobenzoyl chloride, dichlorobenzoyl chloride, monomethylbenzoyl chloride, monochloromethylbenzoyl chloride, dimethylbenzoyl chloride, monomethoxybenzoyl chloride, dimethylbenzoyl chloride, monomethoxybenzoyl chloride, mononitrobenzoyl chloride, phthaloyl chloride, dichlorophthalide, monochlorophthaloyl chloride, dichlorophthaloyl chloride, mononitrophthaloyl chloride and naphthalenecarbonyl chloride.

3. A process according to claim 1, wherein the acid acceptor is a basic organic nitrogen compound selected from the group consisting of a trialkylamine, dialkylcycloalkylamine and dialkylaralkylamine.

4. A process according to claim 1, wherein the acid acceptor is triethylamine.

5. A process according to claim 1, wherein the reaction is effected in the presence of an activator.

6. A process according to claim 5, wherein the activator is a formamide.

7. A process according to claim 1, wherein during the reaction there is added phosgene or thionyl chloride and the reaction is effected at the temperature from about 70° to 160° C.

8. A process according to claim 1, wherein the inert solvent is methylene chloride, ethylene chloride, 1,1,2-trichloroethane, 1,2-dichloropropane, 1,2,3-trichloropropane, chloroform or chlorobenzene.

9. A process according to claim 1, wherein the reaction is carried out at a temperature between about 0° and 160° C.

10. A process according to claim 1, wherein about 1 to 10 moles of the aromatic carbonyl chloride are added dropwise to a solution of 1 mole of the substituted pyridine-1-oxide and of 1 to 10 moles of an amine as the acid acceptor.

11. A process according to claim 10, including adding a formamide and 2 to 5 moles of phosgene or dropwise adding chloride.

12. A process according to claim 1, wherein the reaction mixture formed is subjected to steam distillation.

13. A process according to claim 1, in which $R^2$ is methyl and $R^1$, $R^3$ and $R^4$ are hydrogen the process comprising reacting 3-methyl-pyridine-1-oxide with a benzoyl chloride or phthaloyl chloride in methylene chloride, ethylene chloride, 1,2-dichloropropane, 1,2,3-trichloropropane or chlorobenzene with the addition of triethylamine as acid acceptor.

* * * * *